United States Patent [19]

Sundt et al.

[11] 4,224,351
[45] Sep. 23, 1980

[54] FLAVORING WITH CERTAIN SULPHUR COMPOUNDS

[75] Inventors: Erling Sundt, Pinchat-Geneva; Gunther Ohloff, Bernex, both of Switzerland

[73] Assignee: Firmenich SA, Geneva, Switzerland

[21] Appl. No.: 900,523

[22] Filed: Apr. 27, 1978

Related U.S. Application Data

[60] Continuation of Ser. No. 680,371, Apr. 26, 1976, abandoned, which is a continuation of Ser. No. 304,479, Nov. 7, 1972, abandoned, which is a division of Ser. No. 13,755, Feb. 24, 1970, abandoned.

[30] Foreign Application Priority Data

Feb. 27, 1969 [CH] Switzerland ............... 2928/69
Nov. 3, 1969 [CH] Switzerland ............... 16374/69

[51] Int. Cl.$^3$ .................................. A23L 1/226
[52] U.S. Cl. ........................................ 426/535
[58] Field of Search ............... 426/535; 260/586 R

[56] References Cited

U.S. PATENT DOCUMENTS

| 3,950,429 | 4/1976 | Lamparsky et al. | 426/535 X |
| 3,952,062 | 4/1976 | Lamparsky et al. | 426/535 X |
| 4,034,044 | 7/1977 | Sundt et al. | 260/586 R |

OTHER PUBLICATIONS

Hall et al., III GRAS Substances; Food Technology, vol. 19, Feb. 1965, pp. 151–161, (253–263).
Fluck et al., Composition of Buchu Leave Oil, J. Sci., Food Agric., 12, 1961, pp. 290–292.
Fenaroli's Handbook of Flavor Ingredients, 1971, Edited by Furia et al., Chemical Rubber: Cleveland, p. 55.
Lamparsky et al., P-Methane-8-thiol-3-one, A New Component of Buchu Leave Oil, Tetrahedron Letters, 36, 1971, 3323-3326.
Bedoukian, Progress in Perfumery Material Cosmetics and Perfumery, vol. 88, Apr. 1973, p. 31.
Decision of the Federal Patent Court (Patent Office of the Federal Republic of Germany), 32nd Senate of 10/31/72, 32w(pag) 32/71.
Kleinfield, In Taste and Smell Anything's Possible, The Washington Star, Sunday, Dec. 4, 1977, pp. G-1, G-6.

*Primary Examiner*—Joseph M. Golian
*Attorney, Agent, or Firm*—Pennie & Edmonds

[57] ABSTRACT

New ketone-thiols and their use as perfuming and odor-modifying agents in the manufacture of perfumes and perfumed products, and as flavoring and taste-modifying agents in the preparation of foodstuffs in general and imitation flavors for foodstuffs, beverages, animal feeds, pharmaceutical preparations and tobacco products.

A method for the preparation of said ketone-thiols.

8 Claims, No Drawings

FLAVORING WITH CERTAIN SULPHUR COMPOUNDS

This is a continuation of application Ser. No. 680,371, filed Apr. 26, 1976, now abandoned which in turn is a continuation of application Ser. No. 304,479, filed Nov. 7, 1972, now abandoned, which in turn is a divisional of application Ser. No. 13,755, filed Feb. 24, 1970, now abandoned.

SUMMARY OF THE INVENTION

The invention relates to compounds having the formula

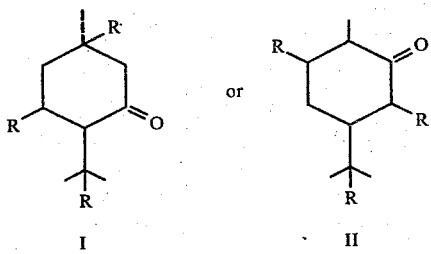

wherein one of the substituents R is —SH and the others are hydrogen. The invention also relates to the use of these compounds as performing and fragrance-modifying agents for the manufacture of perfumes and perfumed products and as flavouring, taste-modifying and taste-enhancing agents for the manufacture of foodstuffs in general and of artificial flavours for foodstuffs, beverages, animal foods, pharmaceuticals and tobacco products. The invention also relates to a method for the preparation of the new compounds.

DESCRIPTION OF THE INVENTION AND OF THE PREFERRED EMBODIMENTS

The compounds of the invention which are named ketonethiols contain a sulphur atom in the molecule and, at first sight, would not appear to be useful in the perfume and flavour industry. In the pure state they develop a powerful unpleasant and agressive smell; however, quite surprisingly, under suitable conditions of dilution they may develop quite pleasant odours and tastes. For instance, depending on the dilution and the presence of other organoleptic materials they may create or intensify the sensation of fruity, green, burnt or roasted notes. They may also remind of aromatic and spicy plants with sometimes garlic-like or mint-like notes. They may also be reminiscent of the taste and odour of black-current leaves and fruit.

The compounds of the invention possess therefore very intersting organoleptic properties and are useful ingredients for the preparation of perfumes and perfumed products. Although they impart in general to such products a very fresh and diffusive top note, they are also capable of conferring a very special character to perfume compositions into which they are added. For instance, they enhance the power of the perfume notes and develop in the compositions a tinge of fruity and greeny character. More particularly, they may impart to said compositions a note of aromatic plants and of black current buds.

The ketone-thiols of the invention can be used as odoriferous ingredients in concentrated or diluted perfumes and in perfumed products such as detergents, cosmetic products, waxes, tooth pastes and lotions and any other products which may be perfumed to make them more attractive commercially.

The proportions in which the new ketone-thiols can be used to produce desirable odoriferous effects can vary within wide limits and depend on the particular effect desired. In the preparation of perfume compositions, for instance, intersting effects can be obtained with proportions as low as 10 ppm to 0.1%. In special cases, the proportion may even reach 1% or higher.

The ketone-thiols of the invention are also very useful flavouring agents in the manufacture of foodstuffs in general and as flavour additives and ingredients for the preparation of imitation flavours and artificial flavour compositions for foodstuffs, beverages, animal feeds, pharmaceutical preparations and tobacco products. They can be used also independently or together with other flavouring agents to modify, improve or enhance the taste of unmanufactured foodstuffs such as fresh fruits and vegetables and of natural flavours. The term foodstuffs used herein has a wide meaning and designates also foodproducts such as for instance chocolate, tea and coffee.

The new compounds can advantageously be used in the preparation of flavours of, for instance, fruits, meat, cheese, seasonings, spices, vinegar and culinary herbs. The proportions in which the flavouring compounds can be used to produce desirable flavouring effects can vary within wide limits. In the flavouring of foodstuffs in general, when the compounds of the invention are used as flavouring agents or additives to modify or to improve the taste and flavour of foodstuffs, beverages, pharmaceutical and tobacco products, very interesting results can be obtained with proportions as low as a few ppm, e.g. 0.1 to 10 ppm of the weight of the product. However, these proportions can be increased beyond 10 ppm, sometimes up to 100 or 1000 ppm when special flavouring effects are sought. In the preparation of imitation flavours or artificial flavouring compositions, proportions ranging from 0.001 to 1% are usable. In special cases they may even reach 10% of the total weight of the composition.

It is to be understood that the concentrations given above with regard to the use of the new ketone-thiols for perfuming and flavouring purposes should not be deemed absolute. In some cases, concentrations higher or lower than these given of the new compounds may be used depending on the specific odoriferous or flavouring effects to be produced.

According to the invention, a method for the preparation of the compounds of formulae I or II, respectively, comprises condensing hydrogen sulphide with a monoolefinic ketone of formula

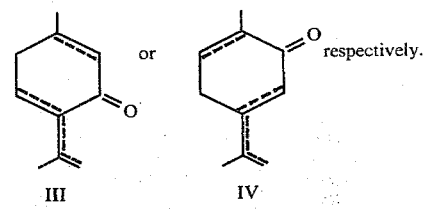

wherein the double bond is indicated by one of the dashed lines.

The above condensation can be carried out according to known methods [see for instance J. Org. Chem. 22

(1957), 980] for example by mixing together the starting materials and allowing the mixture to react at room temperature or at a temperature above or below room temperature. When the condensation is carried out at a temperature above the boiling point of $H_2S$ ($\sim -60°$) it is perferable to operate in a closed vessel which will resist the pressure existing at the operating temperature. Otherwise, undesirable losses of gaseous $H_2S$ might occur. It is preferable to operate at room temperature in a tight vessel since at lower temperatures the reaction time might be too long to be practical and at a higher temperature explosion hazards may be present.

The additional presence in the mixture of small amounts of a basic compound is generally beneficial. The basic compound probably acts as a catalyst of condensation and is advantageously represented by an organic amine such as for instance diethylamine, triethylamine, diisopropylamine, ethylene diamine, butylamine, dibutylamine, tert.-butylamine, piperidine, morpholine, benzylamine, cyclohexylamine and guanidine. Diethylamine and piperidine are preferably used.

The ketones which are used as starting materials in the process of the invention can be obtained commercially either in synthetic racemic form or from natural sources where they may occur in optically active form. The use of optically active ketones may result in the formation of optically active thioketones the organoleptic properties of which do not differ significantly from the inactive ones.

The compounds which result from the application of the process described hereinabove are mixtures of configuration isomers. The stereoisomers can be separated by conventional techniques such as for instance preparative vapour phase chromatography or distillation with a spinning band column. When desired, the isomers can be used separately in the perfume of flavour industry. However, this practice is only justified if the organoleptic properties of the isomers in question are significantly different. In general, it is more economical to use the mixtures of isomers resulting from the process of the invention without separation.

The Examples that follow illustrate the invention with more details. In the said Examples the temperatures are given in degrees centigrade.

EXAMPLE 1

Flavouring composition "tutti frutti"

A basic flavouring composition of the type "tutti frutti" was prepared by admixing the following ingredients:

| Ingredients | Parts by weight |
| --- | --- |
| Vanillin | 20 |
| Allyl caproate | 10 |
| Citral | 15 |
| Amyl butyrate | 35 |
| Orange oil | 50 |
| Ethyl butyrate | 75 |
| Amyl acetate | 185 |
| Ethyl acetate | 185 |
| Lemon oil | 425 |

A test composition (A) and a control composition (B) were prepared by admixing the following components:

| Components | A (parts by weight) | B (parts by weight) |
| --- | --- | --- |
| Base "tutti frutti" | 100 | 100 |
| 95% Ethanol | 880 | 900 |
| 10%* Menthone-8-thiol | 20 | — |
| Total | 1000 | 1000 |

*in 95% ethanol

Afterwards, compositions (A) and (B) were incorporated in a sugar syrup (prepared by dissolving 1 kg. of sucrose in 600 ml. of water) at the concentration of 1 g. of flavour for one liter of syrup.

The finished syrups were tested by a panel of qualified tasters who expressed their views on the value of the flavours used for their preparation. These persons declared unanimously that the taste of the syrup which had been flavoured with composition (A) had a more diffuse and fresher head note than the syrup flavoured with composition (B). By replacing menthone-8-thiol (prepared according to Example 7) by menthone-1-thiol in the example hereinabove similar effects were obtained although slightly less pronounced.

EXAMPLE 2

Mint flavouring composition

A mint base composition was prepared by admixing the following ingredients:

| Ingredients | Parts by weight |
| --- | --- |
| Peppermint oil | 800 |
| Orange oil | 100 |
| Grape-fruit oil | 50 |
| Anis seed oil | 50 |

A test composition (A) and a control flavour composition (B) were then prepared by admixing the following components:

| Components | A (parts by weight) | B (parts by weight) |
| --- | --- | --- |
| Mint base | 100 | 100 |
| 95% Ethanol | 850 | 900 |
| 10%* Menthone-8-thiol | 50 | — |
| Total | 1000 | 1000 |

*in 95% ethanol

Flavours (A) and (B) were then compared in a concentration of 1 g. of flavour for one liter of sugar syrup, exactly as indicated in Example 1. Flavour (A) was judged to have a greener and better diffusing head note than flavour (B).

EXAMPLE 3

Flavouring of beverages and seasoning

The following substances were flavoured with menthone-8-thiol solutions in the amount indicated for 1 kg. of liquid:
(a) Black-current syrup: 0.3 g. of 1% solution*
(b) Raspberry syrup: 0.2 g. of 1% solution*
(c) Vinegar: 0.05 to 0.1 g. of 10% solution*
*in 95% ethanol.

It was found that the taste of the modified syrups had a better diffusing head note and did remind of fresh fruits. The taste of vinegar flavoured as shown was found to be lighter and to have a very interesting garlic-like note.

EXAMPLE 4

Flavouring of instant coffee

A coffee-base was prepared by dissolving relatively bland tasting commercially available spray-dired coffee in boiling Crystal Spring Water. The base solution contained 13 g. of instantly soluble coffee powder for one liter of water. The container used (preferably the lower portion of a glass coffee maker) was absolutely clean; so were the cups and hardware used.

A test sample was prepared by adding 0.025 g. of a 1% solution of menthone-8-thiol in 95% ethanol to 250 ml. of coffee-base. The mixture of coffee-base and flavour was stirred immediately and poured into tasting-cups. The controls were filled with coffee-base containing no flavour added. The tasting was done as soon as possible and, at the latest, within the next 15 min. after filling the cups.

The tasting was performed by a group of experienced tasters who practically unanimously declared that the coffee samples containing the ketone-thiol had a more natural taste than the control and had an improved and enhanced roasted and torrefied note.

EXAMPLE 5

Perfume composition of the Chypre type

A Chypre type composition was prepared by mixing the following ingredients:

| Ingredients | Parts by weight |
| --- | --- |
| Undecenal at 10%* | 20 |
| Dodecanal at 1%* | 30 |
| Methylnonylacetaldehyde at 1%* | 10 |
| Bergamot | 240 |
| Neroli Bigarade | 15 |
| Santal Oriental | 50 |
| Vetyver Bourbon | 40 |
| Orris Concrete | 10 |
| γ-methylionone | 60 |
| Oak Moss absolute | 30 |
| Tarragon | 10 |
| Ylang | 45 |
| Eugenol | 10 |
| Styrax Resinoid at 50%* | 35 |
| Vanillin | 10 |
| Coumarin | 50 |
| Musk ketone | 40 |
| Musk Ambrette | 20 |
| Patchouli | 15 |
| Hydroxycitronellal | 30 |
| Synthetic Rose Oil | 60 |
| Synthetic Jasmine | 60 |
| Rose absolute | 20 |
| Jasmine absolute | 20 |
| Purified natural Civet at 10%* | 30 |
| Labdanum Resinoid at 50%* | 30 |
| Total | 990 |

*in diethyl phthalate

When 10 parts of menthone-8-thiol at 5% in diethyl phthalate were added to 990 parts of the above mixture, a Chypre type composition more powerful than the basic composition and with a fresh and well diffusing head note reminding of black-current buds was obtained.

EXAMPLE 6

Perfume composition of the Chypre type

A Chypre type composition was prepared by mixing the following ingredients:

| Ingredients | Parts by weight |
| --- | --- |
| Undecenal at 10%* | 20 |
| Dodecanal at 1%* | 30 |
| Methylnonylacetaldehyde at 1%* | 10 |
| Bergamot | 240 |
| Neroli Bigarade | 15 |
| Santal Oriental | 50 |
| Vetyver Bourbon | 40 |
| Orris Concrete | 10 |
| γ-methylionone | 60 |
| Oak Moss absolute | 30 |
| Tarragon | 10 |
| Ylang | 45 |
| Eugenol | 10 |
| Styrax Resinoid at 50%* | 35 |
| Vanillin | 10 |
| Coumarin | 50 |
| Musk ketone | 40 |
| Musk Ambrette | 20 |
| Patchouli | 15 |
| Hydroxycitronellal | 30 |
| Synthetic Rose Oil | 60 |
| Synthetic Jasmine | 60 |
| Rose absolute | 20 |
| Jasmine absolute | 20 |
| Purified natural Civet at 10%* | 30 |
| Labdanum Resinoid at 50%* | 30 |
| Total | 990 |

*in diethyl phthalate

When 10 parts of menthone-1-thiol at 10% in diethyl phthalate were added to 990 parts of the above mixture, a Chypre type composition more powerful than the basic composition and with a fresh and well diffusing head note reminding of black-current buds was obtained.

EXAMPLE 7

Preparation of menthone-8-thiol

Pulegone (10 g.; 0.066 Mole, $\alpha_D^{20} = +22°$), liquid $H_2S$ (50 g.; 1.47 Mole) and triethylamine (0.1 g.) were placed in a pressure-proof container at $-80°$. The container was tightly closed and the mixture was left 48 hours at room temperature. After having allowed the excess of $H_2S$ to evaporate, the residue was fractionated in vacuo. 8.7 g. (70%) of menthone-8-thiol, b.p. 57°/0.01 Torr, were thus obtained. It consisted of a mixture, ca. 3:2, of the equatorial and the axial isomers. This mixture was used as such in Examples 1 to 4.

The isomers were separated by preparative vapour phase chromatography (col. "Carbowax" 15%, 2.70 m., 170°, 40 ml. He/min., inject. 250°) and showed the following analytical constants:

| Isomer | cis- | trans- |
| --- | --- | --- |
|  | $\alpha_D^{20} = +32°$ | $\alpha_D^{20} = -22.2°$ |
| Mass spectrum: | 186 (Mol. peak) | 186 (Mol. peak) |
|  | m/e 153 (-SH) | m/e 153 (-SH) |
| NMR spectrum: | 0.96 (3 H, d, J = 7 cps), | 1.02 (3 H, d, badly |
|  | 1.40 (3 H, s), 1.45 | resolved), 1.40 |
|  | (3 H, s), 2.35 (1 H, s) | (6 H, s), 2.30 |
|  | δ ppm | (1 H, s) δppm. |
| IR spectrum: | 1709, 2582 $cm^{-1}$ | 1709, 2583 $cm^{-1}$ |

With regard to the flavouring properties, the axial isomer was found to be more garlic-like and more powerful whereas the aquatorial isomer was judged sweeter and more fruity.

EXAMPLE 8

Preparation of menthone-1-thiol

The reaction was carried out exactly as described in Example 7 and 7.6 g. (0.05 Mole) of piperitone ($\alpha_D^{20} = -44.6°$) were condensed with 3.4 g. (0.1 Mole) of $H_2S$. 4.2 g. (45%) of mentone-1-thiol, b.p. 37°/0.04 Torr, $\alpha_D^{20} = -14°$ were obtained by fractional distillation as a mixture of isomers of configuration. This mixture with a green mint-like, garlic-like and fruity note was used directly as flavouring agent. IR spectrum: 1702, 2560 cm$^{-1}$. Mass spectrum: m/e 186 (Mol. peak) 168 ($-H_2O$), 153 (SH). NMR spectrum: 1.35 (1 H), 1.53 and 1.60 (3 H), 1.85 and 1.95 (6 H).

EXAMPLE 9

Preparation of carvomenthone-4-tiol

The reaction was carried out exactly as described in Example 7 and, from 2.5 g. of carvenone, 17 g. of $H_2S$ and 0.1 g. of triethylamine, a mixture containing 33% of carvomenthone-4-thiol, 60% of starting carvenone, b.p. 65°/0.001 Torr was obtained by fractional distillation. The pure ketone-thiol was obtained by vapour phase chromatography (col. "Carbowax" 15%; 2.7 m.; 170°).

Analysis: Calculated for $C_{10}H_{18}CS$: C, 64.5%; H, 9.74%; S, 17.18%. found C, 63.3%; H, 9.81%; S, 17.14%.

EXAMPLE 10

Preparation of carvomenthone-6-thiol
[1-methyl-4-isopropyl-2-oxo-cyclohexane-6-thiol]

The reaction was carried out as described in Example 7 and; from 2.5 g. of carvotanacetone ($\alpha_D^{20} = +51.4\%$), 17 g. of $H_2S$ and 0.1 g. of triethylamine, 1.16 g., b.p. 69°/0.001 Torr, of carvomenthone-6-thiol, 81% pure, was obtained and used directly as a flavouring agent; the impurity (19%) consisted of starting ketone.

Vapour phase chromatography indicated the presence of two pairs of isomers of the ketone-thiol. The ratio between these pairs was ca. 5:3. The first pair was probably composed of a mixture of the following isomers: trans-(1,4)-trans-(1,6) and cis-(1,4)-cis-(1,6). NMR spectrum: 1.6 (SH), 2.9 (CHSH, m), 0.9-1.0-1.1-1.15 (9 H) The second pair consisted probably of a mixture of the following isomers:

trans-(1,4)-cis-(1,6) and cis-(1,4)-trans-(1,6). NMR spectrum: 1.6 (SH), 3.5 (CHSH, m), 0.9-1.0-1.1-1.2 (9 H) δ ppm.

EXAMPLE 11

Preparation of menthone-5-thiol 1.3 g. (0.009 Mole) of menthenone ($\alpha_D^{20} = -38.7°$), 5 g. (0.15 Mole) of liquid $H_2S$ and 0.03 g. of triethylamine were placed in a pressure-proof container at $-80°$. The container was tightly closed and the mixture was left at room temperature during a week. After the excess of $H_2S$ had been allowed to evaporate, the residue was fractionated in vacuo, b.p. 62°/0.005 Torr. Menthone-5-thiol was thus obtained as a mixture of isomers; yield 22.2%, $\alpha_D^{20} = -20°$. NMR spectrum: 0.88-1.15 (9 H, mixture of d); 1.12 (1 H, s /SH/), 1.7-2.5 (6 H, complex band); 3.65 (1 H, m) δ ppm. IR spectrum: 2560, 1705, 800 cm$^{-1}$. Mass spectrum: m/e 186 (25), 153 (30), 152 (22), 111 (55), 110 (60), 109 (55), 69 (100).

EXAMPLE 12

Preparation of carvomenthone-8-thiol

The reaction was carried out as described in Example 7 and, from 5 g. (0.033 Mole) of dehydrocarvone ($\alpha_D^{20} = -162°$), 0.1 g. of triethylamine and 17 g. (0.5 Mole) of $H_2S$, carvomenthone-8-thiol, b.p. 54°/0.02 Torr, was obtained as a mixture of isomers; yield 19.7%. $\alpha_D^{20} = 1.1°$. NMR spectrum: 0.94 (3 H, d); 1.33 (3 H, s); 1.38 (3 H, s) δ ppm. IR spectrum: 2560, 1700, 775 cm$^{-1}$. Mass spectrum: m/e 186 ($\sim$12%), 111 (65), 75 (100).

EXAMPLE 13

Preparation of menthone-8-thiol

The reaction was carried out as described in Example 7 using 10 g. of isopulegone ($\alpha_D^{20} = 124.2°$), 50 g. of $H_2S$ and 0.1 g. of triethylamine. After fractionating, 69.4% of menthone-8-thiol, $\alpha_D^{20} = -12.0°$, were obtained as a mixture of cis-trans compounds.

We claim:

1. A method for modifying, enhancing or improving the fruity and green organoleptic properties of flavouring compositions, which comprises incorporating in said materials from 0.001 to 10% by weight of a substantially pure compound of the formula

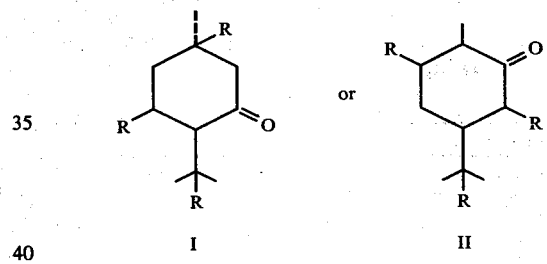

wherein one of the substituents R is —SH and the others are hydrogen.

2. A composition consisting essentially of foodstuffs, beverages, or animal feeds having incorporated therein as a taste and flavour-modifying agent, from 0.1 ppm to 1,000 ppm by weight of a substantially pure compound of the formula

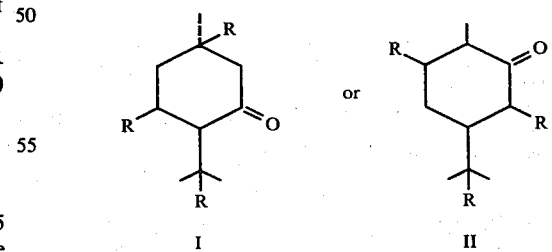

wherein one of the substituents R is —SH and the others are hydrogen.

3. A method for creating, intensifying, modifying, enhancing, or improved a fruity and green taste and flavour of foodstuffs, beverages, or animal feeds, which comprises incorporating in said materials from 0.1 ppm to 1,000 ppm by weight of a substantially pure compound of the formula

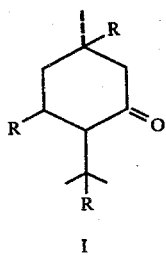 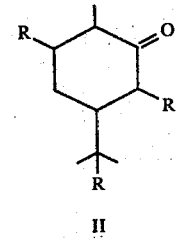

I                         II wherein one of the substituents R is —SH and the others are hydrogen.

4. A method for creating, intensifying, modifying, enhancing or improving a torrified and roasted taste and flavour of natural or instant coffee which comprises incorporating in said materials from 0.1 ppm to 1,000 ppm by weight of a substantially pure compound of the formula

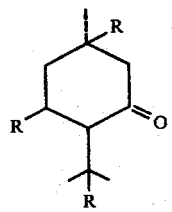 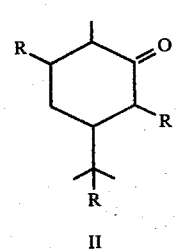

I                         II wherein one of the substituents R is —SH and the others are hydrogen.

5. A method according to claim 1 wherein the substantially pure compound is menthone-8-thiol.

6. A composition according to claim 2 wherein the substantially pure compound is menthone-8-thiol.

7. A method according to claim 3 wherein the incorporated compound is menthone-8-thiol.

8. A method according to claim 4 wherein the incorporated compound is menthone-8-thiol.

* * * * *

UNITED STATES PATENT AND TRADEMARK OFFICE
CERTIFICATE OF CORRECTION

PATENT NO.  : 4,224,351

DATED       : September 23, 1980

INVENTOR(S) : Erling Sundt, Pinchat-Geneva; Gunther Ohloff, Bernex, both of Switzerland It is certified that error appears in the above–identified patent and that said Letters Patent are hereby corrected as shown below:

Column 1, line 34, "animal foods" should read --animal feeds--

Column 1, line 40, "ketonethiols" should read --ketone-thiols--

Column 2, line 7, "intersting" should read --interesting--

Column 3, line 6, "perferable" should read --preferable--

Column 3, line 38, "perfume of flavour" should read --perfume or flavour--

Column 5, line 7, "spray-dired" should read --spray-dried--

Column 7, line 3, "aquatorial" should read --equatorial--

Column 7, line 11, "b.p.37°/0.04" should read --b.p.73°/0.04--

Column 7, line 12, "Torr, $\alpha_D 20=-14°$" should read --Torr. $\alpha_D 20=+14°$--

Column 7, line 22, "carvomenthone-4-tiol" should read --carvomenthone-4-thiol--

UNITED STATES PATENT AND TRADEMARK OFFICE
CERTIFICATE OF CORRECTION

PATENT NO. : 4,224,351

DATED : September 23, 1980

INVENTOR(S) : Erling Sundt, Pinchat-Geneva; Gunther Ohloff, Bernex, both of Switzerland It is certified that error appears in the above-identified patent and that said Letters Patent are hereby corrected as shown below:

Column 7, line 30, "$C_{10}H_{18}CS$" should read --$C_{10}H_{18}OS$--

Column 7, line 36, "cyclohexane-6" should read --cyclohexanone-6--

Column 7, line 38, "+51.4%" should read --+51.4°--

Column 7, line 66, "$\alpha_D 20=-20°$" should read "$\alpha_D 20=-32°$--

Column 8, line 64, "improved" should read --improving--

Signed and Sealed this

Ninth Day of June 1981

[SEAL]

Attest:

RENE D. TEGTMEYER

*Attesting Officer*  *Acting Commissioner of Patents and Trademarks*